United States Patent [19]

Ligon, Jr.

[11] Patent Number: 5,108,468
[45] Date of Patent: Apr. 28, 1992

[54] SWITCHING SYSTEM FOR A MULTIDIMENSIONAL GAS CHROMATOGRAPH

[75] Inventor: Woodfin V. Ligon, Jr., Schenectady, N.Y.

[73] Assignee: General Electric Company, Schenectady, N.Y.

[21] Appl. No.: 674,989

[22] Filed: Mar. 26, 1991

[51] Int. Cl.$^5$ .............................................. B01D 15/08
[52] U.S. Cl. ........................................ 55/67; 55/197; 55/208; 55/270; 55/386
[58] Field of Search ................... 55/67, 197, 386, 208, 55/267, 269, 270

[56] References Cited

U.S. PATENT DOCUMENTS

| | | | |
|---|---|---|---|
| 3,557,533 | 1/1971 | Porter | 55/67 |
| 3,751,880 | 8/1973 | Holm | 55/197 X |
| 3,881,892 | 5/1975 | Gehrke et al. | 55/67 |
| 4,124,358 | 11/1978 | Müller | 55/197 X |
| 4,617,032 | 10/1986 | Wells | 55/67 |
| 4,622,914 | 5/1987 | Hansen et al. | 55/386 |
| 4,654,052 | 3/1987 | Sharp | 55/67 |
| 4,861,358 | 8/1989 | Mueller et al. | 55/386 |
| 4,873,058 | 10/1989 | Arnold et al. | 55/197 X |

Primary Examiner—Robert Spitzer
Attorney, Agent, or Firm—Sudhir G. Deshmukh; James C. Davis, Jr.; William H. Pittman

[57] ABSTRACT

A switching device for a high resolution multidimensional gas chromatograph and a method of supplying a constituent from a component of a sample in a gas chromatograph effluent to a mass spectrometer. A series of open-split interfaces are interposed between a series of gas chromatographs having gas chromatographic columns with different liquid phases. An inert auxiliary fluid such as helium is supplied to the interfaces for carrying the effluent through the various stages of the device. A transfer member of the first interface is initially positioned to a first position to divert the inert fluid and the effluent to atmosphere until the desired component starts eluting from the first gas chromatograph. The transfer member of the first interface is then repositioned to a second position to direct the component and the inert fluid to the second gas chromatograph. A transfer member of the second interface is initially positioned to a first position to divert the inert fluid and the component to atmosphere until the desired constituent starts eluting from the second gas chromatograph. The transfer member of the second interface is then repositioned to a second position to direct the constituent into a mass spectrometer for a qualitative and a quantitative analysis.

29 Claims, 7 Drawing Sheets

SWITCHING SYSTEM FOR A MULTIDIMENSIONAL GAS CHROMATOGRAPH

CROSS REFRENCE TO RELATED APPLICATION

Reference is made to a co-pending application Attorney Docket No. RD-20,642, filed on Mar. 8, 1991, for An Adjustable Open-split Interface for a Gas Chromatograph and a Mass Spectrometer.

FIELD OF THE INVENTION

The present invention generally relates to a multidimensional gas chromatograph, and more particularly concerns a switching system used for a high resolution multidimensional gas chromatograph.

BACKGROUND OF THE INVENTION

The basic chromatography is the separation of components of a sample owing to their differences in solubility or in adsorption in a stationary bed of a material (either liquid or solid). When the sample (moving phase) is a gas, the technique is termed either gas-solid or gas-liquid chromatography, depending on whether the stationary phase is a solid or a liquid. In gas chromatography, a sample is introduced into a carrier gas as a vapor which flows through a chromatographic system. Upon separation by the stationary phase, the sample components travel through the system at different speeds thereby entering a detecting device, attached to the system, at different times. As a result, individual components that are present in the sample may be identified by the detecting device.

A chromatograph such as a gas chromatograph, sometimes hereinafter GC, is an analytical instrument which can separate a gaseous mixture into its various constituent parts. A detecting device such as a mass spectrometer, sometimes hereinafter MS, is an analytical instrument which can qualitatively and quantitatively analyze a gaseous sample to determine its molecular structure. Both gas chromatographs and mass spectrometers have been around for a relatively long time. It has long been recognized that a powerful analytical tool could be obtained by coupling these two instruments. However, combination GC/MS instruments are relatively recent innovations, and continuing research and development is directed towards improving the interface between the gas chromatograph and the mass spectrometer portions of GC/MS instruments.

A typical GC/MS interface includes a tubular transfer line having one end coupled to the output of the gas chromatograph and having its other end extending into a vacuum chamber of the mass spectrometer. An ion source of the mass spectrometer is used to ionize the effluent from the transfer line, and a mass filter of the mass spectrometer is used to filter the ionized components of the gas according to mass. An ion detector within the vacuum chamber of the mass spectrometer detects ions filtered through the mass filter. Finally, a recorded output signal of the detector is studied to determine the chemical structure of the gas sample.

However, gas chromatographs generally operate at atmospheric pressure while mass spectrometers operate at greatly reduced pressures, generally at about $1 \times 10^{-5}$ Torr. To balance such significant differences in pressures between the two devices, the GC/MS interface must provide some means to reduce the pressure of a sample gas leaving the gas chromatograph prior to its introduction into the mass spectrometer. Furthermore, since gas chromatographs operate by sweeping small amounts of sample gas through the GC column, at high volumetric rates of the carrier gas, some means must be found to enrich the concentration of the sample gas relative to the carrier gas before the gas mixture reaches the mass spectrometer. Failure to execute the enrichment step reduces the sensitivity of the mass spectrometer.

Since the gas chromatograph separates the various components of the sample gas or a sample material, the composition of the gas leaving the chromatograph varies with time. Because of the continually changing composition of the gas effluent, any mass spectrometer designed for use with a gas chromatograph must be capable of sweeping rapidly across the mass spectrum, for a swift analysis of the changing composition of the GC effluent.

A wide variety of approaches for interfacing gas chromatographs to mass spectrometers have been tried. The most common approach is a direct connection between the two by means of a capillary tube. The advantage of this type interface is its mechanical stability and the consequent ease with which it can be handled, especially when the chromatographic columns are not changed frequently. There are, however, a wide variety of disadvantages to this method. The major disadvantage of such a capillary restriction is that the sample material, including the solvent, elutes directly into the mass spectrometer source, thereby affecting the sensitivity of the MS. Additionally changing of the GC columns is a laborious and time consuming process as the mass spectrometer vacuum system has to be vented with each GC column change. Another drawback is that all of the gas effluent coming from the gas chromatograph is delivered to the mass spectrometer, thereby potentially overloading the mass spectrometer vacuum system. Thus the mass spectrometers normally designed to accept samples only in nanogram quantites, can be exposed to sample quantities in excess of milligrams. Such an extreme exposure to large amounts of elements causes contamination of the ion source, analyzer and vacuum system of the mass spectrometer, thereby increasing its maintenance cost and reducing the life of filaments used in the variable energy ion source of mass spectrometer.

A direct coupling of the GC to the MS also has an effect on the efficiency of the gas chromatographic separation. By directly coupling the GC to the MS the high vacuum of the mass spectrometer affects the GC column flow rates which results in shifting the GC retention times.

Another common alternative is the so called open-split interface. In its simplest form, one end of an interfacing capillary tube usually made of fused silica is used to provide a flow restriction into the mass spectrometer's GC inlet. The other end of the interfacing capillary tube is telescoped into or placed near the outlet of the GC capillary column. By adjusting the length and the inside diameter of the interfacing capillary tube, a natural vacuum induced flow is maintained to the MS without any permanent or elaborate physical connections between the GC and the interfacing capillary tube. Such an open-split interface has several advantages. The GC column is exposed to atmospheric pressure at its outlet, because it is not sealably connected to the MS. As a result the GC column is not affected by the low pressure of the MS. Secondly, when the aforementioned capillary tube is used as a restrictor, it has been shown that there is virtually no degradation of the chromatographic resolution. Thirdly, if the interfacing capillary tube is held at a constant temperature, by jacketing it in a chamber maintained at a constant temperature, the pressure to which the ion source of the MS is exposed, stays constant even if the GC oven temperature is profiled. Finally, if an accidental breakage of the GC column occurs, such an incident has no effect on the integrity of the MS vacuum.

Even though the aforementioned open-split capillary tube interface overcomes many of the problems associated with the GC/MS interface, it is woefully inadequate in addressing the major problem of solvent diversion which has major impact on the sensitivity and the functionality of the MS. The solvent diversion problem has been partially addressed by enclosing the open-split capillary interface in an evacuated enclosure or an enclosure flooded with an inert fluid, such as helium. A large volume of the inert gas is swept through the interface at the start of the process. Substantially large inert gas flow rate are necessary to flush away the solvent prior to its entry into the MS ion source. However, due to small internal volume of the interface, such large inert gas flow rates result in increasing the pressure within the interface to above the atmospheric pressure, thus increasing the GC retention times and the ion source pressure within the MS. As a result the ion source conditions within the MS may be adversely affected.

The gas chromatographs are also used in multiple stages to separate constituents of a component of the sample that may not be separated by a single stage GC column. Such a technique of separation, called multidimensional gas chromatography, utilizes more than one chromatographic column. Such high resolution multidimensional gas chromatographs (hereinafter MGC) generally have GC columns with different liquid phases. A component may comprise several constituents that cannot be separated by the liquid phase of the chromatographic column through which the component is initially eluted. A constituent is a compound of a desired molecular structure. When a desired component of the sample is at a "peak" in the first GC column, it is switched to the second GC column having a different liquid phase for further separation of the component into its individual constituents.

The major problem faced by the multidimensional chromatography is a lack of a reliable switching scheme that operates at elevated temperatures without affecting the degree of resolution. Several switching schemes have been in use. However these schemes are cumbersome to operate and are mechanically complex. For a general summary, reference is made to Ligon, W., Multidimensional Gas Chromatography: Techniques and Applications, Chapter 3, pages 55-85 of Gas Chromatography: Biochemical, Biochemical and Clinical Applications, edited by Clement, R., ISBN: 0-471-01048-0, 1990 John Wiley & Sons, Inc., incorporated herein by reference. The present invention addresses the switching problems of the MGCs by using the open-split interfaces of the present invention as a switching system.

STATEMENT OF THE INVENTION

In the present invention the aforementioned problems are solved through a method and an apparatus for a switching device of a multidimensional gas chromatograph comprising an interface including a junction means having an inlet, a supply means for introducing an inert auxiliary fluid within the junction means, an aperture means for controlling fluid pressure within the junction means, an outlet for conveying a mixture from the junction means; and a transfer member disposed paritially within the junction means the member being selectively positionable between a first position and a second position, wherein the inlet of the interface is connected to an outlet of a first gas chromatograph, the outlet of the interface is connected to an inlet of a second gas chromatograph and the outlet of the second chromatograph is connected to detecting device, such as a mass spectrometer.

The present invention is also directed to a multidimensional gas chromatograph comprising, a first and at least a second interface each, interface comprising a junction means having an inlet, a supply means for introducing an inert auxilliary fluid within the junction means, an aperture means for controlling fluid pressure within the junction means, an outlet for conveying a mixture from the junction means, a and a transfer member disposed partially within the junction means, the member being selectively positionable between a first position and a second position, wherein when in the first position the effluent is directed to the aperture means and when in the second position the effluent is directed to the outlet.

The present invention is also directed to an analytical apparatus comprising a first and at least a second gas chromatograph, each gas chromatograph further comprising a chromatographic column having an inlet ad an outlet, an injector port of introducing a sample through the chromatographic column of the first chromatograph, a carrier gas supply means connected to the inlet of the first gas chromatograph, a detecting device, a switching device comprising a first and at least a second interface, each interface comprising, a junction means having an inlet, a supply means for introducing an inert auxiliary fluid within the junction means, an aperture means for controlling fluid pressure within the junction means, an outlet for conveying a mixture from the junction means, and a transfer member disposed partially within the junction means, the member being selectively positionable between a first position and a second position, wherein the inlet of the first interface is connected to the otulet of the first gas chromatograph, the outlet of the first interface is connected to the inlet of the second gas chromatograph, the outlet of the second gas chromatograph is connected to the inlet of the second interface, and the outlet of the second interface is connected to the detecting device, a heated chamber for enclosing and maintaining the apparatus at a desired temperature, and a heating means to preheat the inert fluid to a required temperature before entry of the inert fluid into the junction means.

The present invention is further directed to a method of separating a constituent of a component of a sample material present in a gas chromatograph effluent comprising supplying an inert auxiliary fluid from a supply means to a first interface and a second interface wherein the first interface is connected to a first gas chromatograph and to a second gas chromatograph and wherein the second interface is connected to the second gas chromatograph, positioning a transfer member of the first interface disposed partially within a junction means of the first interface to a first position whereby the inert fluid is directed through an aperture means of the first interface to atmosphere, introducing the effluent from the first gas chromatograph into the first interface, entraining the effluent into the inert auxilliary fluid, diverting the entrained effluent to atmosphere through the aperture means of the first interface until the component elutes from the first gas chromatograph, repositioning the transfer member of the first interface to a second positioning for directing the component and the inert fluid to the second gas chromatograph, positioning a transfer member of the second interface disposed partially within a junction means of the second interface to a first position whereby the inert fluid and the component are diverted to atmosphere through an aperture means of the second interface until the constituent elutes from the second gas chromatograph, and repositioning the transfer member of the second interface to a second position for directing the constituent and the inert fluid to an outlet of the second interface.

Other advantages of the invention will become apparent upon reading the following detailed description and appended claims, and upon reference to the accompanying drawings.

BRIEF DESCRIPTION OF THE DRAWINGS

For a more complete understanding of this invention reference should now be had to the embodiments illustrated in greater detail in the accompanying drawings and described below by way of examples of the invention.

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

DETAILED DESCRIPTION OF THE PREFERRED EMBODIMENT

Figure 1:
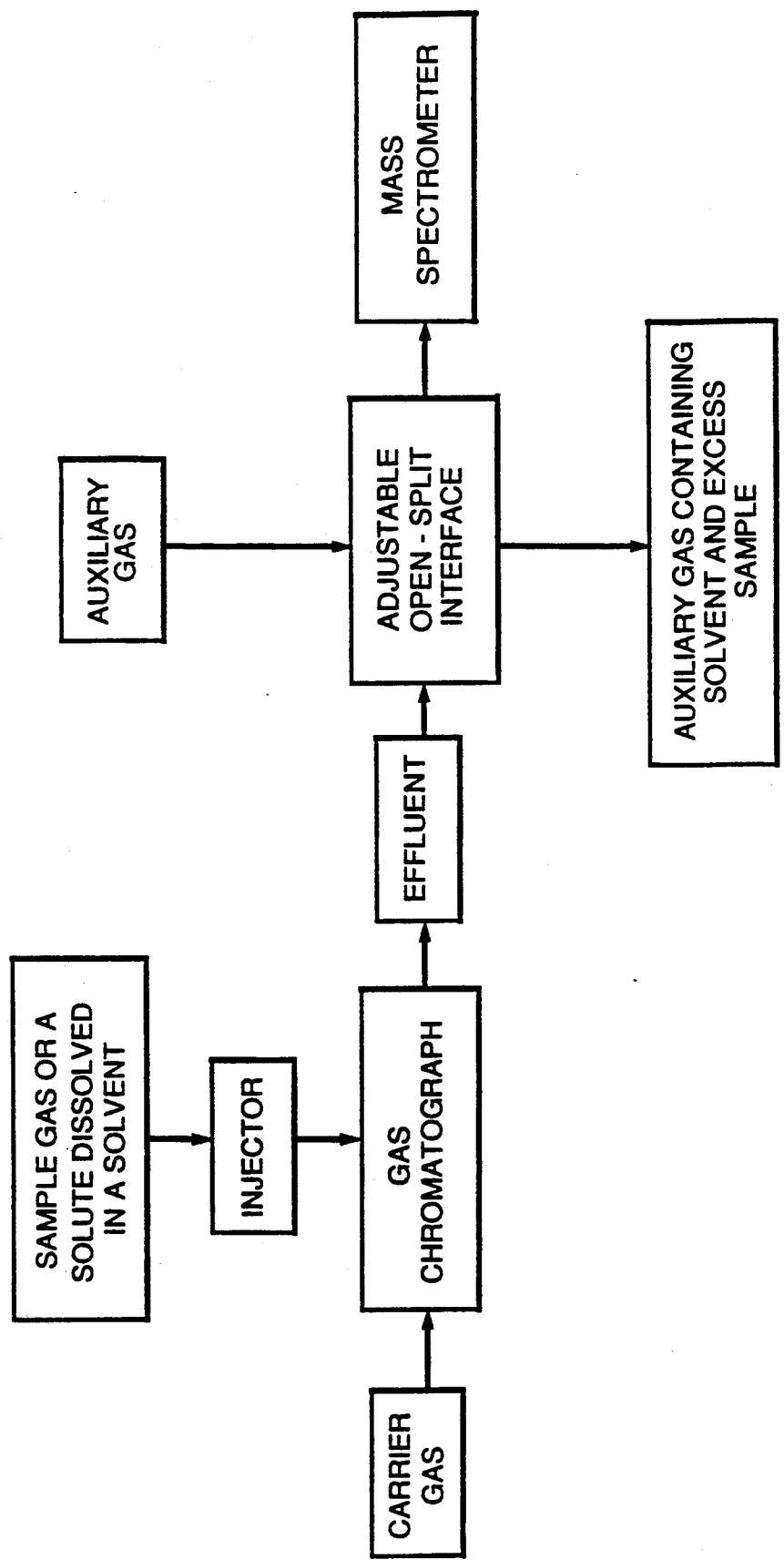
FIG. 1 is a block diagram depicting the major components of the apparatus of the present invention.

Turning to FIG. 1 there is shown a block diagram, generally pointing out the path of travel of the sample material being analyzed by the apparatus of the present invention. The material to be analyzed is initially isolated in the gas chromatograph. Gas chromatographic separation involves the process of using a carrier gas to force a sample gas through a column containing a separation medium. Typically such a column is made from a fused silica tubing having its inner diameter coated with a polymeric material (stationary liquid phase) such as polydimethylsiloxane. Generally the inner diameter of the tubing is about 0.25 to about 0.32 millimeters. The carrier gas is generally an inert gas, such as helium. Once the sample gas has been "carried" through the chromatographic column by the carrier gas, the function of the carrier gas has been served and its presence in high concentration impedes identification of the various sample gas components by a detecting device such as a mass spectrometer.

Alternatively, a sample may be dissolved in a solvent and then injected by an injector into the gas chromatographic column wherein dissolved solute is "carried" by the GC carrier gas, such as helium, to the mass spectrometer. The function of the aforementioned solvent is only to facilitate efficient transport of the sample to the GC, however, its presence in the ionization block of the MS severely effects the sensitivity of the MS.

The adjustable open-split interface of the present invention allows efficient removal of the solvent from the sample solute, thereby providing a substantially solvent free solute into the mass spectrometer.

The gas chromatograph may be of any conventional design, such as a Hewlett-Packed Model 5890 GC.

The solute substantially free from the solvent is ionized, filtered and analyzed by any conventional mass spectrometer such as a JEOL (Japanese Electronics Optical Laboratories) Model SX102.

The adjustable open-slit interface may be also used in the MGC used during a high resolution gas chromatography.

Figure 2:
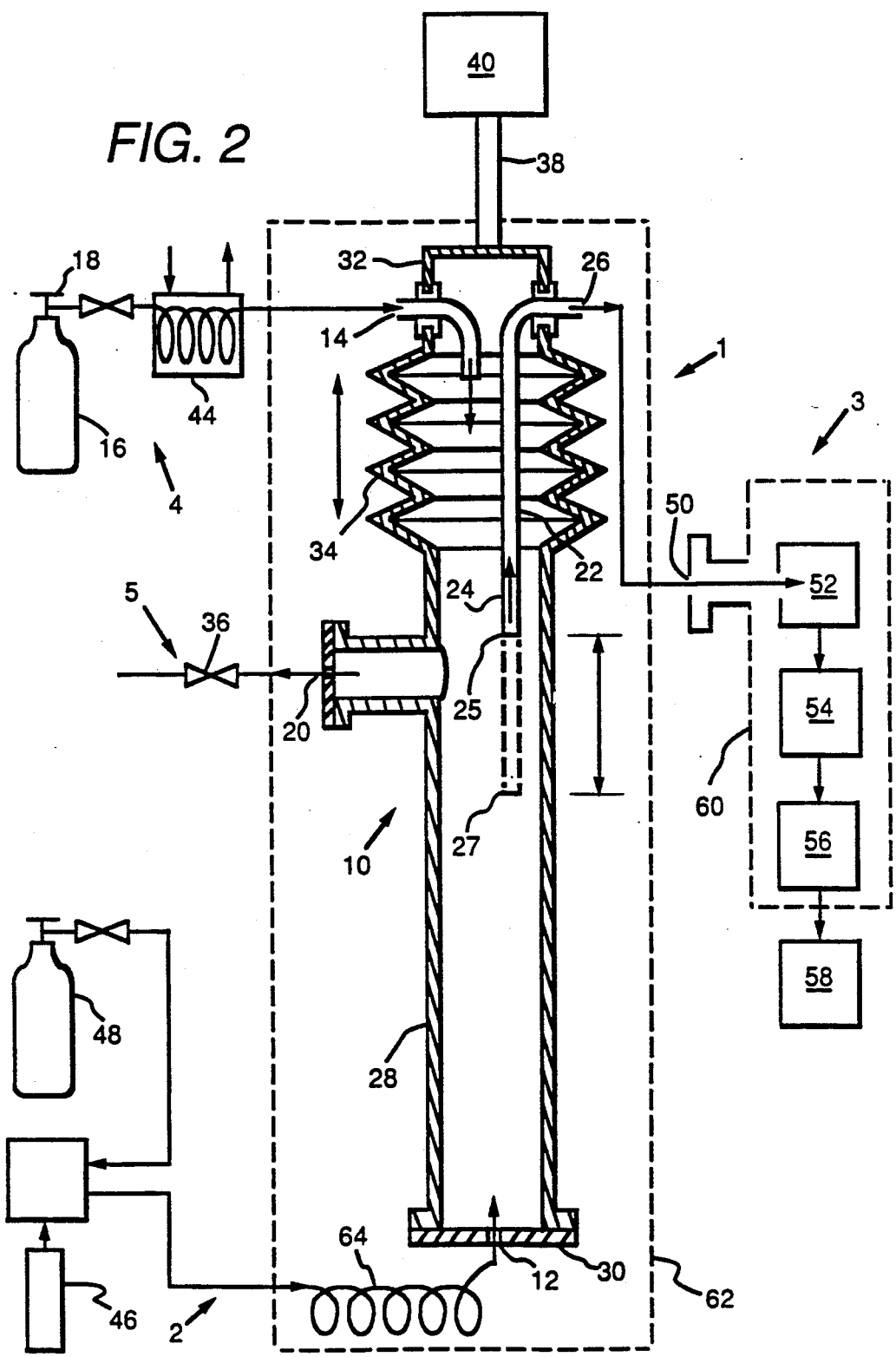
FIG. 2 is a view of an apparatus of the preferred embodiment.

Turning now to FIG. 2, there is shown an apparatus of the preferred embodiment of the invention. The adjustable open-split interface generally indicated by numeral 1, connects at least one gas chromatograph 2 with a detecting device 3, typically a mass spectrometer. Interface 1 includes a junction means, generally indicated by numeral 10, comprising a hollow close ended conduit 28 having a first end 30 and a second end 32. Preferabl an inert material such as a glass lined stainless steel is used in the fabrication of junction means 10 so that it has a negligible effect on the solute sample material being analyzed by the detecting device 3. In the preferred embodiment of the present invention, junction means 10 was fabricated from a glass lined tubing supplied by SGE (Scientific Glass Engineering) Company, Austin, Tex. However to those skilled in the art, alternatives to the aforementioned product will be apparent. An inlet 12, provided near first end 30 of conduit 28, is connected through a compression fitting such as a Swagelok ® fitting to chromatograph 2. Junction means 10 may be provided additional inlets for connecting additional gas chromatographs.

A port 14, provided near second end 32 of conduit 28, is connected to supply means of an inert auxiliary fluid supply, generally indicated by a numeral 4. Preferably an inert auxiliary fluid introduced from vessel 16 through port 14 is the same as GC carrier gas supplied from vessel 48, such as helium. An inert auxiliary fluid regulating means 18 are used to control the flow of the inert auxiliary fluid from vessel 16. A heating means 44, may be interposed between an inert auxiliary fluid regulating means 18 and port 14 of junction means 10, for controlling the temperature of the inert auxiliary fluid, before its entry into junction means 10. The source of heat within heating means 44 may be provided, for example, by electrically heated resistance coils. However, it will be obvious to those skilled in the art to use some other means for heating the inert auxiliary fluid to a desired temperature.

Interface 1 is further provided with an aperture means, generally indicated by numeral 5. Aperture means 5 connected to an exhaust port 20, preferably located between first end 30 and second end 32 of junction means 10, permits controlling of pressure within junction means 10 by a regulator 36 located in an exhaust line of aperture means 5 open to the atmosphere. It is contemplated that, if required, the exhaust line may be connected to a vacuum system, not shown, to expose junction means 10 to less than atmospheric pressure.

At least one outlet of interface 1 is provided by at least one hollow elongated transfer member 22 having outlet 26 at one end and an intake 24 at the other end. The outlet is provided for conveying a mixture from interface 1 to detecting device 3. The mixture comprises the inert auxiliary fluid, the effluent from the GC or a combination thereof. The transfer member 22 coaxially disposed within conduit 28, has a portion of it, nearer to outlet 26, projecting outwardly from near second end 32 of conduit 28. Transfer member 22 is preferably a fused silica capillary tube having an internal diameter of about 0.1 to about 0.2 millimeters. However, it is comtemplated that those skilled in the art may utilize some other types of capillary tubes. The internal diameter of the transfer member 22 should be adjusted to maintain a level of vacuum at which detecting device 3 operates.

Second end 32 of conduit 28 is provided with a bellows 34, having a closed end. Transfer member 22 enter conduit 28 from near a crown of bellows 34 and it is affixed to the crown of bellows 34. Transfer member 22 is provided a reciprocal motion by compression and expansion of bellows 34. As a result of such a reciprocal motion, intake 24 of transfer member 22 may be selectively positioned between a first position 25 and a second position 27, shown by dotted lines in FIG. 2. When transfer member 22 is in first position 25 the GC effluent is directed to aperture means 5 and when transfer member 22 is in the second position 27 the GC effluent is directed to outlet 26.

Junction means 10 and a chromatographic column 64 of GC 2 are preferably enclosed within a heated chamber 62 maintained at a desired temperature. Junction means 10 may be provided a plurality of inlets for connecting more than one GC chromatograph to interface 1. Junction means 10 may be also provided with at least one entry port for injecting chemical reagents into the GC effluent entering junction means 10 for a post column derivatization. The post column derivatization is a verification step used for establishing identity of the component present in the GC effluent. A chemical reaction is carried out between the separated component exiting from the GC column and the chemical reagent before the reacted component enters the mass spectrometer. For example, deuterium oxide may be used as the chemical reagent to establish identity of a hydroxyl group.

A driving means 40, preferably powered by electromechanical means such as a solenoid, is connected to a driver end of an actuating lever 38. The driven end of actuating lever 38 is affixed to the crown of bellows 34. Preferably the energization of driving means 40 is controlled through a software program executed by a computer. However, any other conventional driving means such as manually applied power are also contemplated.

Junction means 10 is connected to detecting device 3, by coupling outlet 26 to an input orifice 50 of detecting device 3. Types of detecting devices suitable for the present invention are a mass spectrometer, flame ionization detector, photoionization detector, electron capture detector, radiometric detector, thermal conductivity detector, flame photometric detector, nitrogen phosphorus detector (FID type), thermionic ionization detector, infrared spectrophotometric detector, atomic absorption spectrometric detector, helium ionization detector, chemiluminescent nitrogen specific detector, the preferred detecting device being a mass spectrometer. It is noted that while using some of the aforementioned detectors, regulator 36 of aperture means 5 may have to be partially closed to increase pressure within junction means 10 to force the mixture from junction means 10 into detecting device 3. Typically outlet 26 is sealably and flexibly coupled, by means of a flexible tubing, to detecting device 3 to allow freedom of movement to transfer member 22. Preferably a conventional mass spectrometer, shown in FIG. 2, is used as detecting device 3. Such a conventional mass spectrometer comprises a variable energy ion source 52, a mass filter 54, an electron multiplier 56 and an analyzing computer 58. Some of the components of the mass spectrometer such as variable energy ion source 52, mass filter 54 and electron multiplier 56 are enclosed within an evacuated chamber 60. It should be understood that the present also contemplates use of any other sutiable type of mass spectrometer.

Turning now to the operation of the preferred embodiment as shown in FIG. 2, a sample containing various components is dissolved in a solvent, and then injected through an injector 46 into gas chromatograph 2. The solvent containing the dissolved sample is then carried by the carrier gas. The gas chromatograph effluent exiting from chromatographic column 64 is fed through inlet 12 into open-split interface 1 of the present invention. The inert auxiliary fluid. introduced through port 14 into conduit 28, exits out of aperture 20 to the atmosphere. The pressure of the inert auxiliary fluid within conduit 28 may be controlled by adjusting regulating means 36 of aperture means 5. If so desired, regulating means 36 may be connected to a vacuum source, to draw off the inert auxiliary fluid and the GC effluent. However, it is preferable to exhaust the inert auxiliary fluid at normal atmospheric pressure. As the gas chromatograph effluent enters conduit 28, it is exhausted through exhaust port 20 to the atmosphere, along with the inert auxiliary fluid supplied through port 14. Generally the initial GC effluent flow from the GC column is richer in the solvent, and by exhausting the initial GC effluent flow to atmosphere, the effect of the solvent on the MS is minimized. Before the aforementioned initial GC effluent flow is introduced into conduit 28, intake 24 of transfer member 22 is preferably positioned at first position 25 near exhaust port 20, thereby directing the GC effluent to the atmosphere through exhaust port 20 and aperture means 5.

By energizing driving means 40, bellows 34 may be compressed or expanded for providing a reciprocal motion to transfer member 22. As shown by the dotted lines in FIG. 2, intake 24 of transfer member 22 may be located at either first position 25 or second position 27. When intake 24 of transfer member 22, positioned at first position 25, is repositioned to second position 27, the gas chromatograph effluent is directed through outlet 26 of transfer member 22 to orifice 50 of the detecting device 3. The inner diameter of transfer member 22 has a significant impact on the degree of vacuum within detecting device 3. By keeping the inner diameter of transfer member 22 narrow, for example at less than about 0.2 millimeter, the interface of the present invention supplies the GC effluent to the MS under invariant conditions. By positioning intake 24 at intermediate positions between first position 25 and second position 27, detecting device 3 may be incrementally supplied with the inert auxiliary fluid, the gas chromatograph effluent or a mixture of the two.

When a mass spectrometer is used as detecting device 3, the material within the gas chromatograph effluent entering through orifice 50, is converted into an ion beam by variable energy ion source 52. The aforementioned ion beam then passes through mass filter 54 for selecting ions of a desired mass to charge ration and for filtering out the remaining nonselected ions. The current, produced by the ion beam of the selected ions, is then provided with a gain by electron multiplier 56. By providing such a gain, the quality of an analysis of the selected ions is significantly improved. Computer 52 the qualitatively and quantitatively analyzes the signals generated by the selected ions for porviding the desired analysis of the sample introduced in the GC.

Figure 3:
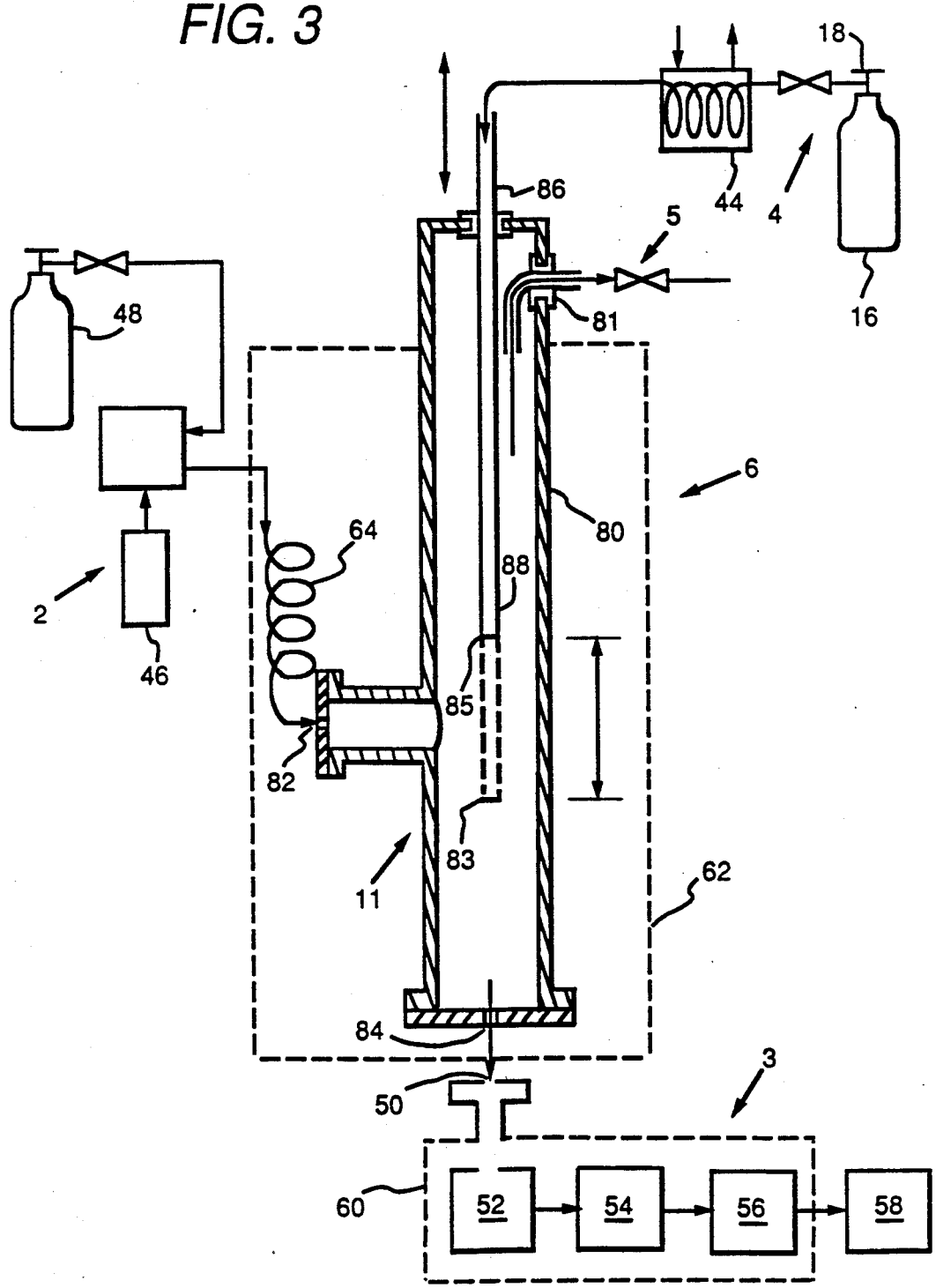
FIG. 3 is a view of an apparatus of another embodiment of the present invention.

FIG. 3 illustrates another embodiment of the present invention showing an adjustable open-split interface, generally indicated by numeral 6. As so far described some of the implements of FIG. 3 are substantially like those of FIG. 2. The two differ primarily in that FIG. 3 provides a different style of an open-split interface than in FIG. 2. All the components substantailly same between FIG. 2 and FIG. 3 are represented by same numerals.

A manifold 80 of interface 6 having a first end and a second end is provided with an outlet 84 at the first end. Outlet 84 is connected to a conventional detecting device 3, such as a mass spectrometer. An inlet 82 is provided on a side of manifold 80 to admit the effluent from the gas chromatograph generally indicated by numeral 2. An exhaust port 81 located near the second end of manifold 80 is connected to aperture means 5. A hollow coaxially disposed elongated transfer member 86 partially telescopes within manifold 80 and has its exposed end connected to supply means of an auxiliary inert fluid supply, generally indicated by a numeral 4. A supply end 88 of elongated transfer member 86 may be selectively positioned at a first position 83 near the first end of manifold 80 or at a second position 85 near the second end of manifold 80. Transfer member 86 may be directed to first position 83 or to second position 85 by providing it with reciprocal motion through a driving means not shown in FIG. 3. However to those skilled in the art, it will be apparent to use driving means such as an electrically operated solenoid for providing the required reciprocal motion. When transfer member 86 is in first position 83, the GC effluent is directed to aperture means 5 and when transfer member 86 is in second position 85 the GC effluent is directed to outlet 84.

In operation, as shown in FIG. 3, supply end 88 of elongated transfer member 86 is initially positioned at first position 83 and the inert auxiliary fluid is introduced into manifold 80 through supply end 88 of transfer member 86 and allowed to escape to the atmosphere by passing through aperture means 5. When the gas chromatograph effluent is introduced through inlet 82, the initial solvent rich effluent is carried off to the atmosphere by the inert auxiliary fluid. At a desired moment, elongated transfer member 86 is repositioned to second position 85 by the driving means, not shown, thereby moving supply end 88 from near outlet 84 to near inlet 82. Such a displacement of elongated member 86 is shown by the dotted line in FIG. 3. The GC effluent entering through inlet 82 is now urged by auxiliary inert fluid 16 towards outlet 84. The GC effluent is then introduced into detective device 3 through orifice 50 of detecting device 3 connected to outlet 84.

Figure 4:
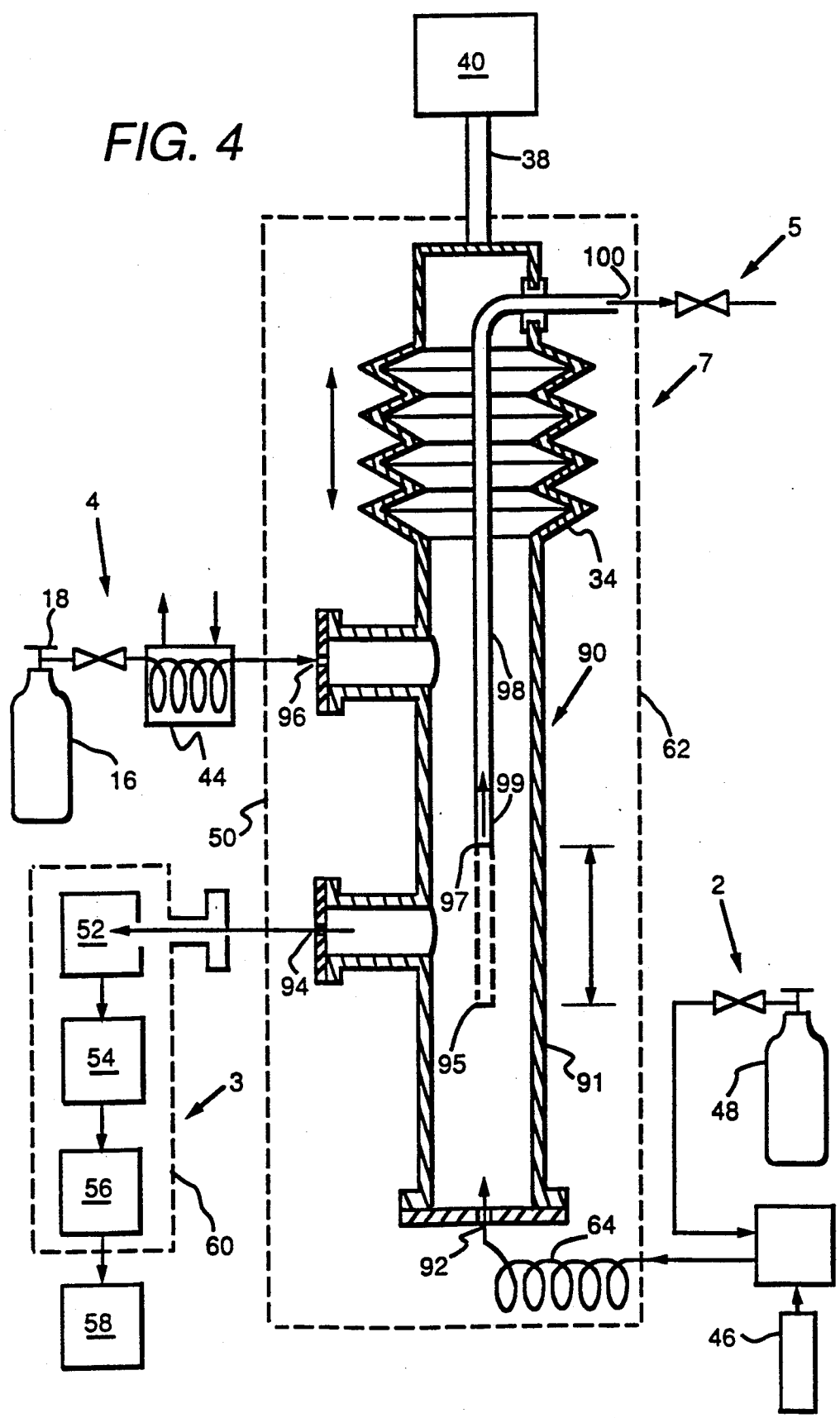
FIG. 4 is a view of an apparatus of yet another embodiment of the present invention.

FIG. 4 illustrates yet another embodiment of the present invention showing an open-split interface, generally indicated by numeral 7. As so far described some ot the implements of FIG. 4 are substantially like those of FIG. 2. The two differ primarily in that FIG. 4 provides a different style of an open-split interface than in FIG. 2. All the components substantially same between FIG. 2 and FIG. 4 are represented by same numerals. Interface 7 comprises a junction means, generally indicated by numeral 90 and formed by a close ended conduit 91. An inlet 92 positioned at a first closed end of conduit 91 is connected to the gas chromatograph, generally indicated by numeral 2. A second closed end of conduit 91 is provided a bellows 34 operated by driving means 40 connected through an actuating lever 38 to the crown of bellows 34.

Conduit 91 is further provided with a port 96 preferably positioned near the second closed end of conduit 91 and connected to supply means, generally indicated by numeral 4 for introducing the inert auxiliary fluid within junction means 90. An outlet 94 preferably positioned near the first end of conduit 91 is connected to orifice 50 of detecting device, generally indicated by numeral 3.

At least one coaxially disposed elongated transfer member 98 is partially disposed within condut 91. Transfer member 98 is further provided an intake end 99 and an exhaust end 100, wherein exhaust end 100 is connected to aperture means, generally indicated by numeral 5. Intake end 99 may be selectively positioned at a first position 95 near inlet 92 or to a second position 97 near outlet 94. Transfer member 98 affixed to bellows 34 may be directed to first position 95 or to second position 97 by providing a reciprocal motion to it through an actuation of bellows 34 by driving means 40. However it will be apparent to those skilled in the art to use some other means of providing the reciprocal motion to transfer member 98. When transfer member 98 is in first position 95, the GC effluent is directed to aperture means 5 and when transfer member 98 is in second position 97 the GC effluent is directed to outlet 94.

In operation, as seen in FIG. 4, intake end 99 of elongated transfer member 98 is initially positioned at first position 95 and the inert auxiliary fluid is introduced into conduit 91 throgh port 96 and allowed to escape to the atmosphere by passing through aperture means 5 connected to exhaust end 100. When the gas chromatograph effluent is introduced through inlet 92, the initial solvent rich effluent is carried off to atmosphere by the inert auxiliary fluid. At a desired moment, elongated transfer member 98 is repositioned to second position 97 by driving means 40, thereby placing intake end 99 from near inlet 92 to near outlet 94. Such a displacement of elongated member 98 is shown by the dotted line in FIG. 4. The GC effluent entering through inlet 92 is now urged by the inert auxiliary fluid towards outlet 94. The GC effluent is then introduced into detective device 3, for the analysis, through orifice 50 of detecting device 3 connected to outlet 94.

Figure 5:
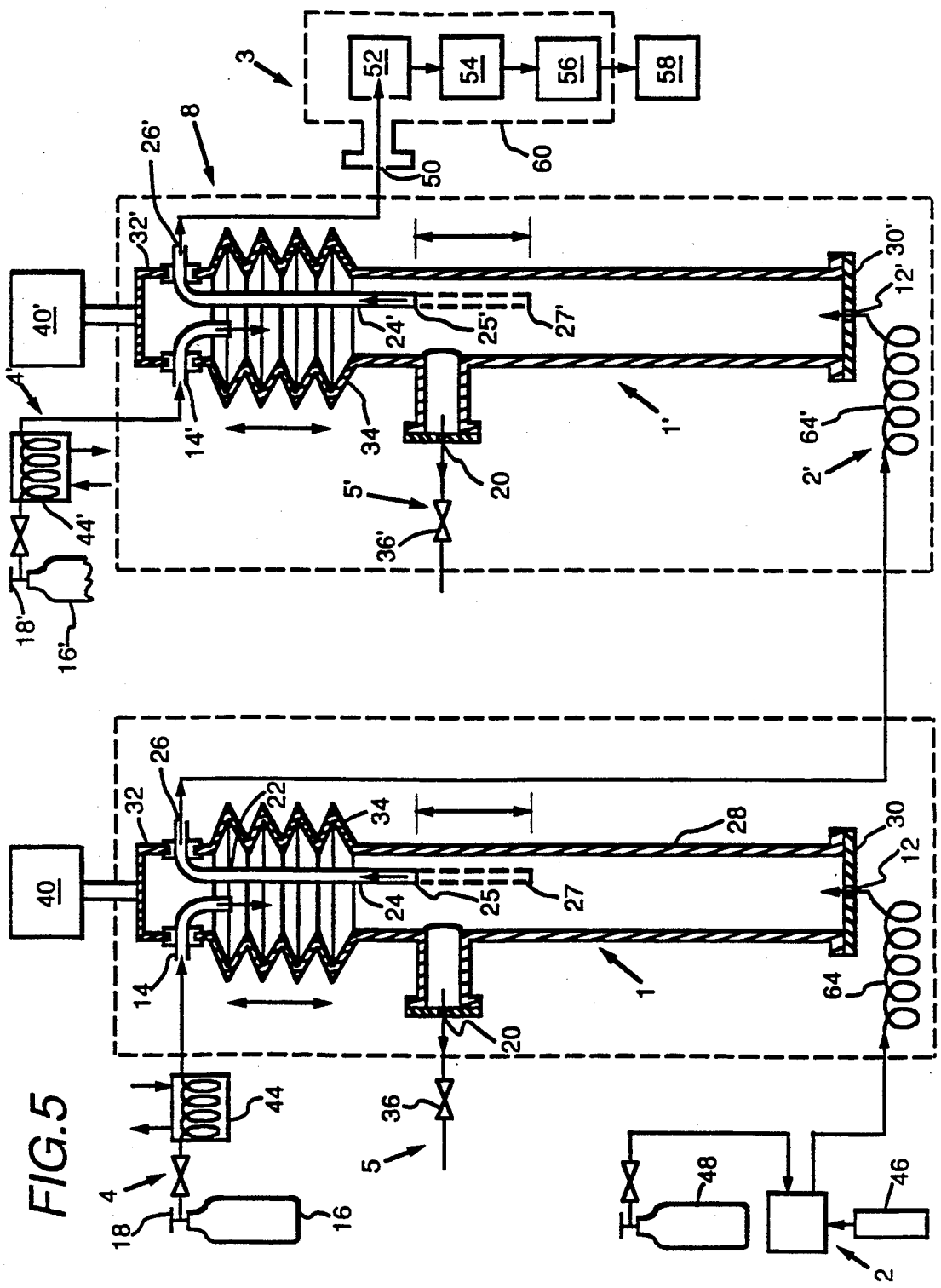
FIG. 5 is a view of an apparatus of still another embodiment of the present invention.

FIG. 5 illustrates another embodiment of the present invention showing an improved multidimensional gas chromatograph, generally indicated by numeral 8. As so far described some of the implement of FIG. 5 are substantially like those of FIG. 2. However FIG. 5 provides the multidimensional gas chromatography apparatus used for significantly improving the power of resolution of a gas chromatograph. All the components substantially the same between FIG. 2 and FIG. 5 are represented by same numerals. Multidimensional gas chromatographs are very useful in separating individual components of a sample material having same solubility in a liquid phase of a gas chromatographic column used during chromatography. A desired peak component from the sample separated by a first chromatographic column and containing the individual constituents having same solubility can then be passed through a second gas chromatographic column having a different liquid phase capable of separating the individual constituents.

Multidimensional gas chromatograph apparatus comprises a series of adjustable open-split interfaces alternately connected to a series of gas chromatographs. FIG. 5 shows a 2-dimensional gas chromatograph apparatus having two interfaces interposed between two gas chromatographs. However it is understood that the same principle may be also extended to a two dimensional gas chromatograph apparatus having a single interface connected between two gas chromatographs, an outlet of the second chromatograph being connected with a detecting device, such as a mass spectrometer. Referring to FIG. 5 a first stage of apparatus 8 is a first interface generally indicated by numeral 1 and a second stage of apparatus 8 is a second interface generally indicated by numeral 1'. Inlet 12 of first interface 1 is connected to an outlet of a first chromatograph generally indicated by a numeral 2. Outlet 26 of first interface 1 is connected to an inlet of chromatographic column 64 of second gas chromatograph 2'. It should be noted that injector 46 and the carrier gas are only provided to first chromatograph 2. In addition to the carrier gas, the inert auxiliary fluid supplied to interface 1 and 1' is also used for carrying the chromatograph effluent through 2-dimensional gas chromatograph 8. The importance of the inert auxiliary fluid becomes more significant in a multidimensional gas chromatograph having several interfaces, because the momentum initially supplied by the carrier gas may not be sufficient to carry the gas effluent all the way to a detecting device. Regulators 36 and 36' of aperture means 5 and 5' respectively may be partially closed to provide above atmospheric pressure within junction means 10 and 10'. Inlet 12' of second interface 1' is connected to receive the chromatograph effluent from chromatographic column 64' of a second gas chromatograph generally indicated by numeral 2'. It should be noted that the liquid phases used in chromatographic columns 2 and 2' may differ in their ability to separate various constituents of the components present in the sample introduced into gas chromatograph 2. Outlet 26' of second interface 1' is connected to orifice 50 of a detecting device generally indicated by numeral 3. Transfer member 24 and 24' of interface 1 and 1' respectively may be independently positioned by an acutation of driving means 40 and 40' respectively or transfer members 24 and 24' may be simultaneously positioned by an actuation by a single driving means, not shown in FIG. 5. If desired, interfaces 1 and 1' and GC columns 64 and 64' may be placed in the heated chambers maintained at desired temperatures.

Turning now to the operation of the embodiment as shown in FIg. 5, the inert auxiliary fluid from supply means 4 and 4' is supplied to first interface 1 and second interface 1' respectively. Transfer member 24 is positioned at first position 25 to direct flow of the inert auxiliary fluid to atmosphere through aperture means 5. A sample containing various components is dissolved in a solvent, and then injected through injector 46 into gas chromatograph 2. The solvent containing the dissolved sample is then carried by the carrier gas through gas chromatograph 2. The gas chromatograph effluent existing from the outlet of chromatographic column 64 of gas chromatograph 2 then enters into first interface 1 through inlet 12. The effluent from gas chromatograph 2 is then entrained in the inert auxiliary fluid present in interface 1. The entrained effluent is diverted to atmosphere through aperture means 5 until the desired component starts eluting from chromatographic column 64. Preferably a detecting device, such as a mass spectrometer, interposed between the outlet of gas chromatograph 2 and inlet 12 of interface 1 is used to detect the presence the desired component in the gas chromatogragh effluent. However, to those skilled in the art, other ways of detecting the presence of the component may be obvious. When the component starts eluting from chromatographic column 64, transfer member 24 is repositioned to second position 27 for directing the component and the innert auxiliary fluid to outlet 26 of interface 1. The component and the inert auxiliary fluid exiting from outlet 26 are fed into the inlet of chromatographic column 64' of second chromatograph 2'. Transfer member 24' of second interface 1' is positioned at first position 25' to divert the component and the inert auxiliary fluid to atmosphere through aperture means 5' until the desired constituent starts eluting from the outlet of gas chromatograph 2'. As stated earlier a detecting device may be employed to detect presence of the desired constituent in the effluent. The liquid phase of gas chromatographic column 64' may be tailored to separate the desired constituent from the component entering gas chromatograph 2'. Transfer member 24' is then repositioned to second position 27' to direct the desired constituent to outlet 26' of interface 2'. Typically outlet 26' delivers the desired component to detecting device 3, such as a mass spectrometer for performing a qualitative and a qualitative analysis. Thus by passing the gas chromatograph effluent through two interfaces interposed by two gas chromatographic columns, the components of the sample are separated into their consitituents. It should be noted that the power of resolution may be enhanced even further by providing a series of interfaces alternated by a series of gas chromatographs.

The present invention will be further understood from the illustration of specific examples which follow. These examples are intended for illustrative purposes only and should not be construed as limitation upon the broadest aspects of the invention.

EXAMPLES

Figure 6:
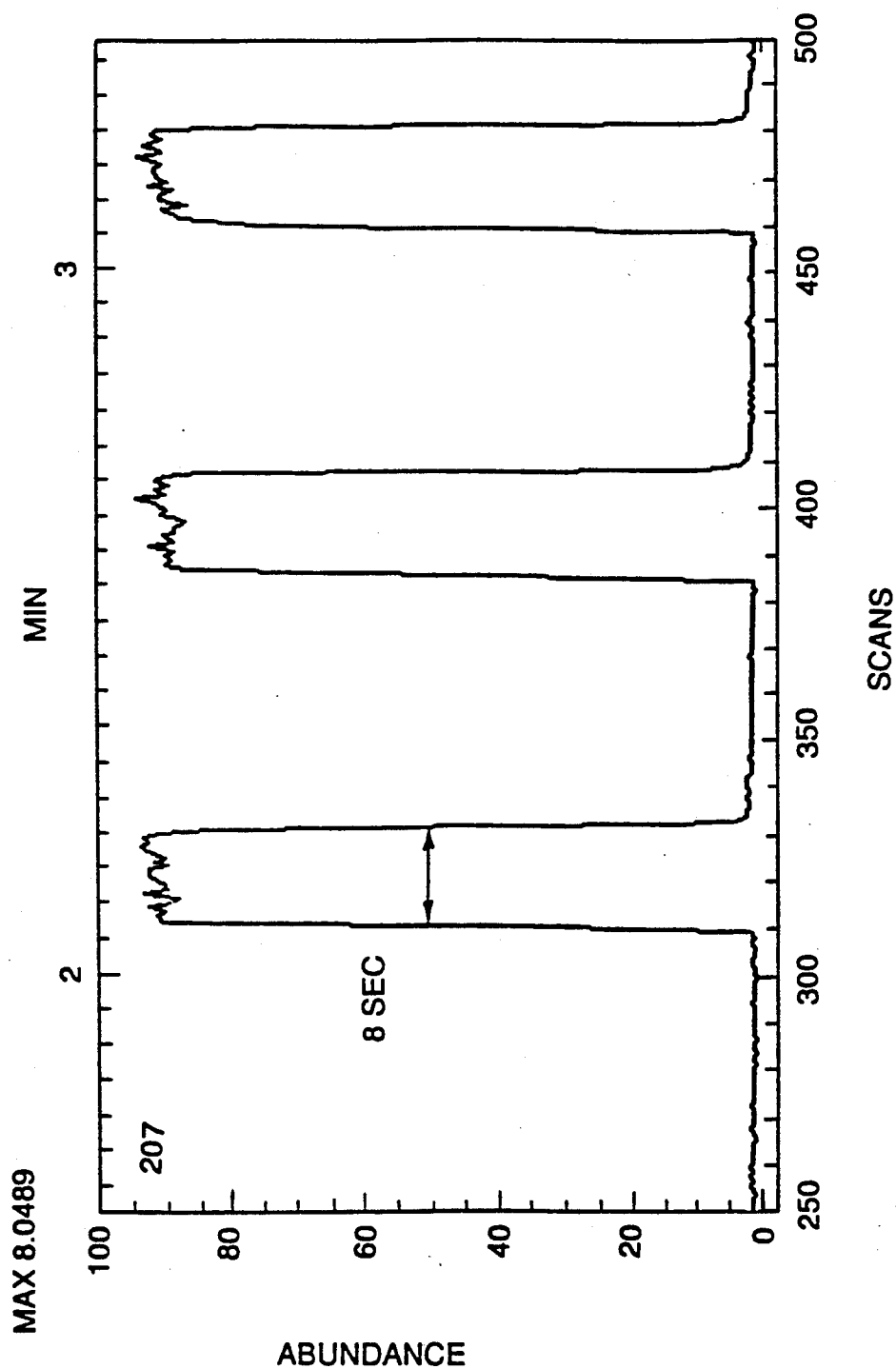
FIG. 6 is scan showing responses of the apparatus of the preferred embodiment.
Figure 7:
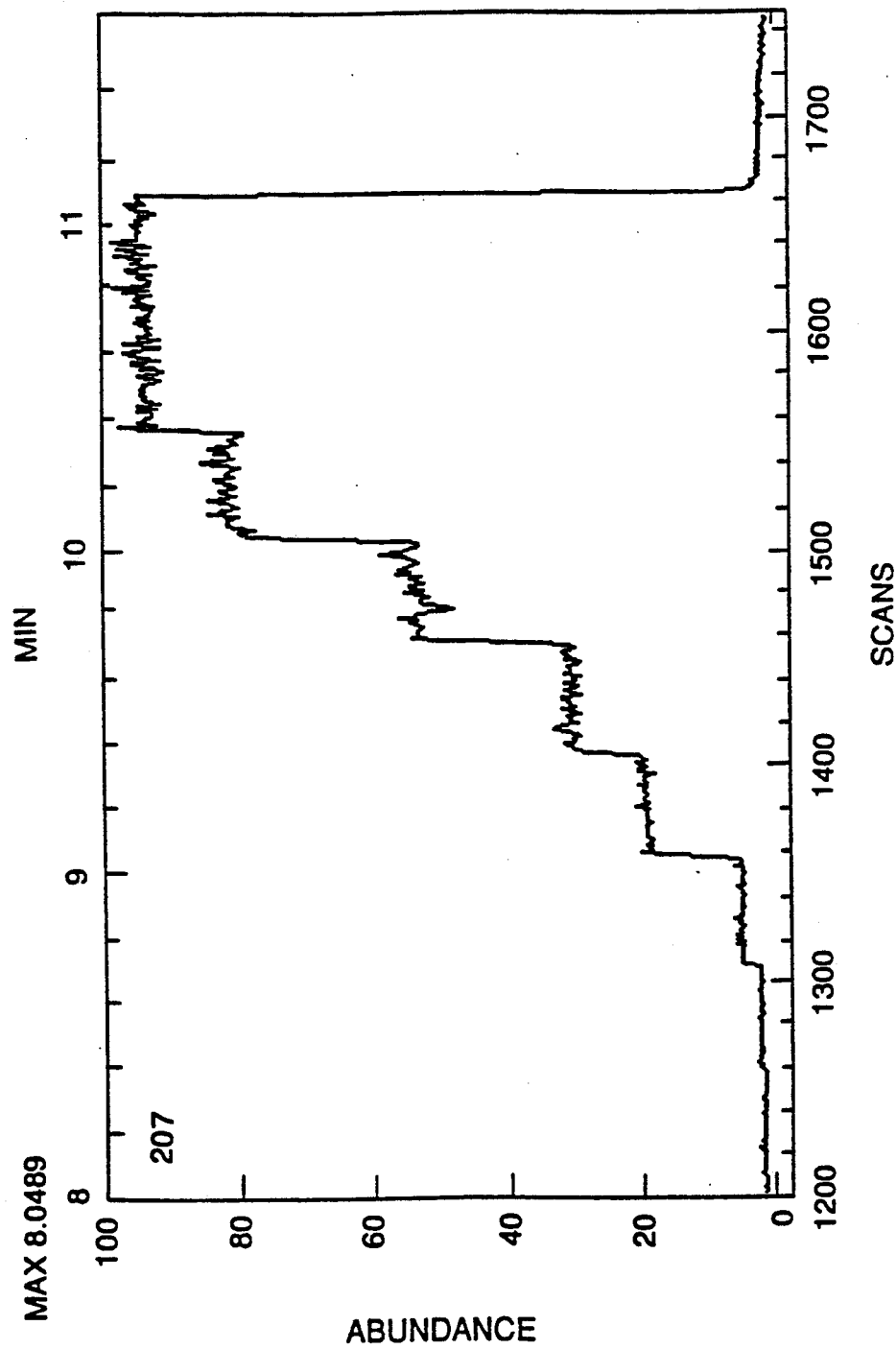
FIG. 7 is a scan showing incremental switching response of the apparatus of the preferred embodiment.

FIG. 6 represents a scan showing the on/off switching ability, the switching speed and the switching reproducibility of interface 1, shown in FIG. 2. FIG. 7 represents a scan showing the partial switching ability of interface 1 of FIG. 2 achieved through incremental positioning of transfer member 22 between first position 25 and second position 27. The GC effluent used for both the scans had a mass of 207 at a GC effluent flow of about 2 milliliters per minute and inert auxiliary fluid flow at about 2.5 milliliters per minute. The gas chromatograph was operated at about 300° C. The distance between first position 25 and second position 27 was about 2.0 milliliters.

While particular embodiments of the invention have been shown, it will be understood of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

What is claimed is:

1. A method of separating a constituent of a component of a sample material present in a gas chromatograph effluent comprising:
   supplying an inert auxiliary fluid from a supply means to a first interface and a second interface wherein said first interface is connected to a first gas chromatograph and to a second gas chromatograph and wherein said second interface is connected to said second gas chromatograph;
   positioning a transfer member of said first interface disposed partially within a junction means of said first interface to a first position whereby said inert fluid is directed through an aperture means of said first interface to atmosphere;
   introducing said effluent from said first gas chromatograph into said first interface;
   entraining said effluent into said inert auxiliary fluid;
   diverting said entrained effluent to atmosphere through said aperture means of said first interface until said component elutes from said first gas chromatograph;
   repositioning said transfer member of said first interface to a second position for directing said component and said inert fluid to said second gas chromatograph;
   positioning a transfer member of said second interface disposed partially within a junction means of said second interface to a first position whereby said inert fluid and said component are diverted to atmosphere through an aperture means of said second interface until said constituent elutes from said second gas chromatograph; and
   repositioning said transfer member of said second interface to a second position for directing said constituent and said inert fluid to an outlet of said second interface.

2. The method according to claim 1 further comprising introducing said constituent to a detecting device for a qualitative and a quantitative analysis.

3. The method according to claim 2 wherein said detecting device is a mass spectrometer.

4. The method according to claim 1 further comprising heating and maintaining said first chromatograph, said second chromatograph, said first interface, and said second interface at desired temperatures.

5. The method according to claim 1 wherein said inert auxiliary fluid is helium.

6. A switching device for a multidimensional gas chromatograph comprising:
   an interface including a junction means having an inlet;
   a supply means for introducing an inert auxiliary fluid within said junction means;
   an aperture means for controlling fluid pressure within said junction means;
   an outlet for conveying a mixture from said junction means; and
   a transfer member disposed partially within said junction means, and member being selectively positionable between a first position and a second position, wherein said inlet of said interface is connected to an outlet of a first gas chromatograph, said outlet of said interface is connected to an inlet of a second gas chromatograph.

7. The device according to claim 6 wherein an outlet of said second gas chromatograph is connected to a detecting device.

8. The device of claim 7 wherein said detecting device is a mass spectrometer.

9. The device according to claim 6 wherein when said transfer member is in said first position said mixture is directed to said aperture means and when said transfer member is in said second position said mixture is directed to said outlet.

10. A switching device for a multidimensional gas chromatograph comprising:
    a first and at least a second interface each said interface comprising;
    a junction means having an inlet;
    a supply means for introducing an inert auxiliary fluid within said junction means;
    an aperture means for controlling fluid pressure within said junction means;
    an outlet for conveying a mixture from said junction means; and
    a transfer member disposed partially within said junction means, said member being selectively positionable between a first position and a second position.

11. The device according to claim 10 wherein when said transfer member is in said first position said mixture is directed to said aperture means and when said transfer member is in said second position said mixture is directed to said outlet.

12. The device according to claim 10 wherein said inlet of said first interface is connected to an outlet of a first gas chromatograph, said outlet of said first interface is connected to an inlet of a second gas chromatograph, an outlet of said second gas chromatograph is connected to said inlet of said second interface, and said outlet of said second interface is connected to detecting device.

13. The device of claim 12 wherein said detecting device is a mass spectrometer.

14. The device according to claim 10 wherein said junction means further comprises:
    a conduit having a first end and a second end wherein said inlet is located near said first end;
    an exhaust port located between said first end and said second end and connected to said aperture means;
    a port located near said second end and connected to said supply means; and
    a driving means for directing said transfer member to said first position or to said second position.

15. The device according to claim 14 wherein said driving means further comprises:
    a bellows affixed to said conduit near said second end and having said transfer member fixedly attached thereto; and
    an actuating lever having a driven end connected to said bellows and a driver end connected to a driving means for providing a reciprocal motion to said transfer member by an actuation of said bellows by said driving means.

16. The device according to claim 14 wherein said driving means is manually powered.

17. The device according to claim 14 wherein said driving means is powered by electro-mechanical means controlled through a software program executed by a computer means.

18. The device according to claim 14 wherein said first position is near said aperture means and said second position is near said first end.

19. The device according to claim 14 wherein said outlet of said second interface, located on said transfer member of said second interface, is sealably and flexibly coupled to said detecting device to allow said reciprocal motion of said transfer member of said second interface.

20. The device according to claim 10 wherein said junction means further comprises:
a manifold having a first end and second end wherein said outlet is located near said first end;
an exhaust port located near said second end and connected to said aperture means;
said inlet located between said first end and said second end;
said supply means connected to said transfer member; and
a driving means for directing said transfer member to said first position or to said second position.

21. The device according to claim 20 wherein said first position is near said first end and said second position is near said second end.

22. The device according to claim 10 wherein said junction means is of inert material.

23. The device according to claim 22 wherein said inert material is glass lined stainless steel.

24. The device according to claim 10 wherein said aperture means is further provided with a regulating means to expose said junction means to varying pressures.

25. The device according to claim 10 wherein said transfer member is a capillary tube.

26. The device of claim 10 further comprising a heated chamber for enclosing and maintaining said device at a desired temperature.

27. The device of claim 10 further comprising heating means to preheat said inert fluid to a required temperature before entry of said fluid into said junction means.

28. An analytical apparatus comprising:
a first and at least a second gas chromatograph, each said gas chromatograph further comprising a chromatographic column having an inlet and an outlet;
an injector port for introducing a sample through said chromatographic column of said first chromatograph;
a carrier gas supply means connected to said inlet of said first gas chromatography;
a detecting device;
a switching device comprising a first and at least a second interface each said interface comprising, a junction means having an inlet; a supply means for introducing an inert auxiliary fluid within said junction means, an aperture means for controlling fluid pressure within said junction means, an outlet for conveying a mixture from said junction means, and a transfer member disposed partially within said junction means, said member being selectively positionable between a first position and a second position, wherein said inlet of said first interface is connected to said outlet of said first gas chromatograph, said outlet of said first interface is connected to said inlet of said second gas chromatograph, said outlet of said second gas chromatograph is connected to said inlet of said second interface, and said outlet of said second interface is connected to said detecting device;
a heated chamber for enclosing and maintaining said apparatus at a desired temperature; and
a heating means to preheat said inert fluid to a required temperature before entry of said inert fluid into said junction means.

29. The analytical apparatus of claim 28 wherein said detecting device is a mass spectrometer comprising a variable energy ion beam source, a mass filter means for selecting ions of a desired mass to charge ratio coming from said ion beam source, an electron multiplier means for adding a gain to current of said selected ions, and a computer means for a qualitatively and quantitatively analyzing said selected ions.

* * * * *